(12) United States Patent
Salvant

(10) Patent No.: US 12,185,943 B2
(45) Date of Patent: *Jan. 7, 2025

(54) CURLED SUTURE DEVICE APPARATUS AND METHOD

(71) Applicant: SMART SUTURES, LLC, Mandeville, LA (US)

(72) Inventor: Thomas Salvant, Covington, LA (US)

(73) Assignee: SMART SUTURES, LLC, Mandeville, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/123,534

(22) Filed: Mar. 20, 2023

(65) Prior Publication Data

US 2023/0218292 A1 Jul. 13, 2023

Related U.S. Application Data

(60) Continuation of application No. 16/906,930, filed on Jun. 19, 2020, now Pat. No. 11,607,214, which is a
(Continued)

(51) Int. Cl.
*A61B 17/06* (2006.01)
*A61B 17/00* (2006.01)
(Continued)

(52) U.S. Cl.
CPC .... *A61B 17/06166* (2013.01); *A61B 17/0469* (2013.01); *A61B 17/06066* (2013.01);
(Continued)

(58) Field of Classification Search
CPC .... A61B 17/06066; A61B 2017/00004; A61B 2017/0608; A61B 2017/1132
See application file for complete search history.

(56) References Cited

U.S. PATENT DOCUMENTS

2009/0216268 A1* 8/2009 Panter .............. A61B 17/06166
606/228
2012/0143226 A1* 6/2012 Belson ............... A61B 17/0057
606/139
(Continued)

*Primary Examiner* — Ashley L Fishback
(74) *Attorney, Agent, or Firm* — KEATY LAW FIRM LLC; Thomas S. Keaty

(57) ABSTRACT

The present invention provides a suturing device to minimize interference and obstructions during intricate surgeries. The curled suture device is significantly shorter than traditional suturing kits by featuring a needle attached to a specially manufactured thread incorporating a stopping mechanism preceding an angular, semi-rigid portion of thread followed by a curled portion of thread arranged in a corkscrew configuration. The stopping mechanism halts the movement of the thread as the needle and thread intermediate the needle and stopping mechanism is pulled through the suture point, securing the remainder of the thread for access. The semi-rigid portion of thread is thereby utilized in conjunction with its curled portion of thread, allowing for the user's unabated access to the corkscrew configuration to form a ready-made knot, minimizing interference and obstruction during surgery. The thread may be manufactured to form an additional semi-rigid and curled portions of thread upon creation of a knot.

4 Claims, 10 Drawing Sheets

Related U.S. Application Data division of application No. 15/679,978, filed on Aug. 17, 2017, now Pat. No. 10,722,230, which is a continuation-in-part of application No. 15/394,578, filed on Dec. 29, 2016, now abandoned.

(60) Provisional application No. 62/274,145, filed on Dec. 31, 2015.

(51) Int. Cl.
*A61B 17/04* (2006.01)
*A61B 17/11* (2006.01)

(52) U.S. Cl.
CPC ............... *A61B 2017/00004* (2013.01); *A61B 2017/00867* (2013.01); *A61B 2017/0477* (2013.01); *A61B 2017/0608* (2013.01); *A61B 2017/06171* (2013.01); *A61B 2017/06176* (2013.01); *A61B 2017/1132* (2013.01)

(56) References Cited

U.S. PATENT DOCUMENTS

| | | | | |
|---|---|---|---|---|
| 2015/0297241 | A1* | 10/2015 | Yodfat | A61B 17/12109 606/200 |
| 2016/0220371 | A1* | 8/2016 | Keane | A61F 2/2442 |
| 2020/0107932 | A1* | 4/2020 | Rabito | A61F 2/2466 |

* cited by examiner

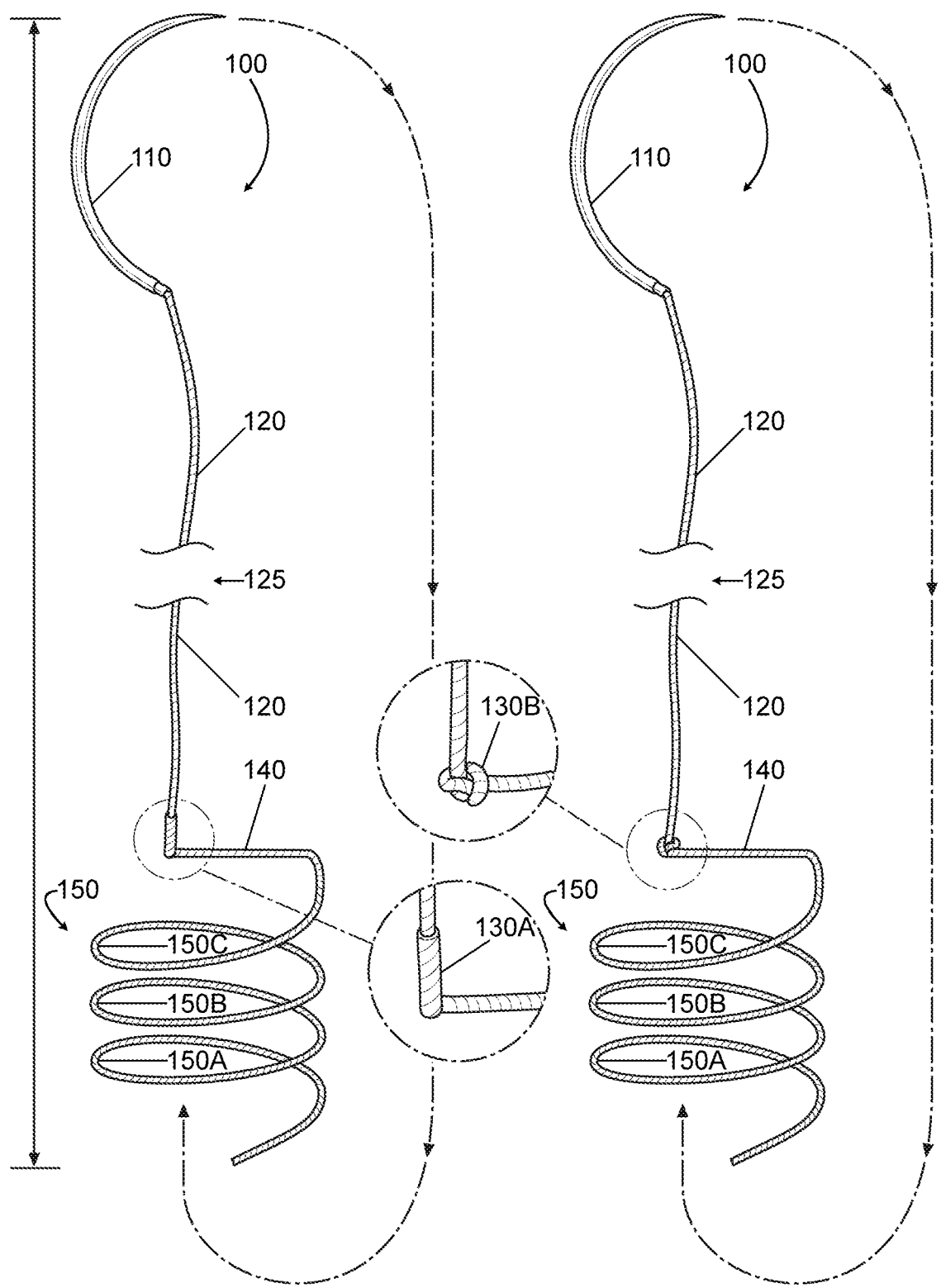
FIG. 2A  FIG. 2B

CURLED SUTURE DEVICE APPARATUS AND METHOD

CROSS-REFERENCE TO RELATED APPLICATIONS

This application is a continuation of co-pending application Ser. No. 16/906,930, filed on Jun. 19, 2020, which is a divisional of application Ser. No. 15/679,978, filed on Aug. 17, 2017, now U.S. Pat. No. 10,722,230, issued Jul. 28, 2020, which is a continuation-in-part of application Ser. No. 15/394,578, filed on Dec. 29, 2016, now abandoned, which claims the benefit of provisional application Ser. No. 62/274,145, filed on Dec. 31, 2015, the full disclosures of which are incorporated by reference herein and priority of which are hereby claimed.

BACKGROUND OF THE INVENTION

The present invention provides a suturing device to minimize interference and obstructions during intricate surgeries. The curled suture device is significantly shorter than traditional suturing kits, by provision of a needle attached to a specially manufactured thread incorporating a stopping mechanism that precedes an angled, semi-rigid portion of thread, followed by a curled portion of thread arranged in a corkscrew configuration. The stopping mechanism halts the movement of the thread as the needle and thread intermediate the needle and stopping mechanism is pulled through the suture point, securing the remainder of the thread for access by the user. The semi-rigid portion of thread is thereby utilized in conjunction with its curled portion of thread, allowing for the user's unabated access to the corkscrew configuration to form a ready-made knot, minimizing interference and obstruction during surgery. The thread may be manufactured to form an additional semi-rigid and curled portion of thread upon creation of a knot.

In laparoscopic surgery or other similar procedures, the healthcare provider may be required to work on the inside of a particular cavity of the body of the patient. In working in this cavity, there may be instruments inserted into the patient to allow the healthcare provider to perform the procedure, such as a camera, instruments holding the cavity open in an appropriate manner, and multiple sutures and associated thread to allow for repair of the interior tissue. Use of these instruments ultimately crowds the healthcare provider's working space, and interferes with a smooth and efficient surgical procedure.

By providing the curled suture device of the present invention, with a specially manufactured thread that allows for a ready-made knot or multiple ready-made knots, the healthcare provider is able to perform the suturing with only one hand, while his or her second hand may secure, for example, the camera utilized in the procedure. Further, by eliminating the need to manually create a knot from standard suturing thread, the thread may be significantly shortened from needle to tip, and thus free up space within the surgical cavity. The angled, semi-rigid portion of the thread and its corresponding curled portion of the thread, in conjunction, centers the suturing area in the appropriate section of the surgical cavity, which allows the healthcare provider to operate within the scope of his or her view within the surgical cavity. The arrangement would also allow for fewer adjustments to the position of the camera, which in turn decreases disruption of both the procedure and physicality of the patient. The stopping mechanism further facilitates these advantages, as it allows for the healthcare provider to more easily create the knot by ensuring the curled section of the suture remains in the appropriate place during the suturing process. Additionally, in allowing for the healthcare provider to control both the suture and sutured tissue with a single hand, the healthcare provider is able to adjust the final suture spot as necessary without additional disruption of the tissue and surgical cavity.

As outlined below, various references provide for curls on suturing thread. However, the prior art does not provide for a stopper mechanism on the thread, nor any angled, semi-rigid portion of the thread, to more effectively suture the desired area when used in conjunction with the curled portion of the thread. The prior art therefore does not effectively aid the healthcare provider in the laparoscopic procedure. The prior art additionally does not contemplate the varied stopper mechanisms that should be taken into account when tailoring the suture device for specific surgical procedures.

For example, U.S. Publ. No. 2009/0216268, published Aug. 27, 2009 by Gideon G. Panter, discloses a suture for facilitating tying of knots that includes a length of suture material fixed to a needle. At least part of the length of the suture material is resiliently biased to a coiled state that is able to be straightened under applied tension but which returns to its coiled state when released. In use, part of the suture material is drawn through a region of tissue so that portions of the suture material lie on opposite ends of the tissue. A knot is then formed in the suture material by passing one of the portions through at least one resiliently-formed coil formed in the other of the portions, and pulling tight the suture material.

This Panter suture discusses the use of a coiled thread to assist in the creation of a knot, but does not provide for a stopper mechanism on the thread, nor any angled, semi-rigid portion of thread that may be used in conjunction with the provided coil. Such a configuration would be necessary to create the knot in the appropriate spot of the suturing device, and would also assist the healthcare provider in pulling the tissue regions together without disruption when suturing.

U.S. Pat. No. 5,454,834, issued Oct. 3, 1995 to Manfred Boebel et al., discloses a surgical suture material provided with a thread and, in some cases, a needle to allow formation of a knot with the greatest possible security while expending little effort, even in situations where space is limited—for example, during an endoscopic operation. The suture material has at least one inherently stable coil, loop, or similar preformed featured in at least one initial preformed section of its length. Another section of the thread or an end of the thread can be threaded or guided through this preformed feature for the purpose of forming a loop and/or knot. The preformed section can take the form of a preformed feature with an approximately spiral shape, for example.

However, this Boebel patent, like the above-disclosed Panter suture, does not provide for a stopper mechanism on the thread nor any angled, semi-rigid portion of thread that may be used in conjunction with the provided coils for effective suturing. Further, the Boebel patent requires multiple preformed sections (i.e., coils) of thread, present concurrently with one another, which simply serves to further crowd the suturing space instead of simplifying and streamlining the suturing process, as is intended by the present invention.

There is accordingly a need for a curled suture device that aids in reducing interference during a surgical procedure by provision of a specially manufactured suturing thread providing a ready-made knot or multiple ready-made knots, incorporating an angled, semi-rigid portion of the thread and a corresponding curled portion of the thread, and which is in part further facilitated by a stopping mechanism in the thread that aids in the creation of the knot by securing the ready-made knot(s) in the appropriate area during the procedure. In allowing for the healthcare provider to suture the appropriate tissue with only one hand, the healthcare provider may also easily adjust the location of the suture and upcoming knot within the surgical cavity, which allows for reduced interference within the surgical cavity.

SUMMARY OF THE INVENTION

The present invention provides a suturing device to minimize interference and obstructions during intricate surgeries, such as laparoscopic surgeries. The curled suture device is significantly shorter than other suturing kits currently available for use, as it features a suturing needle attached to the end of a specially manufactured suture thread that incorporates a specially placed stopping mechanism immediately preceding an angled, semi-rigid portion of the thread, followed by a corresponding curled portion of the thread arranged in a corkscrew configuration, forming several loops before coming to an end. The stopping mechanism serves to halt the movement of the thread as the needle and thread intermediate between the needle and stopping mechanism is pulled through the suture point, securing the remainder of the thread on the first side of the tissue being sutured. Immediately following the stopping mechanism, an angled, semi-rigid portion of the thread is utilized in conjunction with its corresponding curled portion of the thread, allowing for the healthcare provider's unabated access to the corkscrew configuration that allows for a ready-made knot in the suture device, to aid in minimizing interference and obstruction during surgery. The suture thread may be manufactured to automatically form an additional angled, semi-rigid portion of the thread and a corresponding curled portion of the thread upon creation of a previous knot, allowing the aforementioned process to be duplicated to create additional knots as necessary for the healthcare provider's requirements. The length of the entire device, from the tip of the suture needle to the end of the specially manufactured suture thread, is of a length significantly shorter than typical suture kits, which may stretch up to several feet long, which also aids in reducing interference and obstruction during the surgical process.

The present invention solves existing problems in the surgical field, namely providing a suturing device that aids in suturing pieces of tissue by providing a pre-existing knot formation, and allowing for the formulation of additional ready-made knots, encompassing an angled, semi-rigid portion of thread and a corresponding curled portion of thread, that aids the healthcare provider in creating a knot during the process of suturing, and by also providing additional features, such as varied stopping mechanisms and varied lengths of thread, to further streamline and simplify the suturing process.

BRIEF DESCRIPTION OF DRAWINGS

Reference will now be made to the drawings, wherein like parts are designated by like numerals, and wherein:

FIG. 2A is a schematic view of the curled suture device according to an embodiment of the present invention;

FIG. 2B is a schematic view of the curled suture device according to a second embodiment of the present invention;

DETAILED DESCRIPTION OF THE DRAWINGS

Figure 1A:
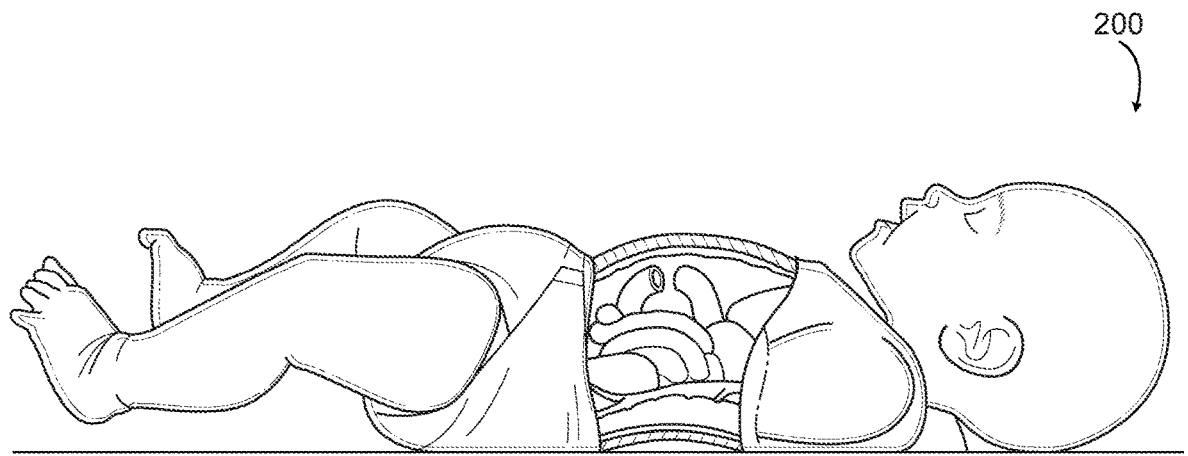
FIG. 1A is a view of a patient with a schematic depiction of a surgical area.
Figure 1B:
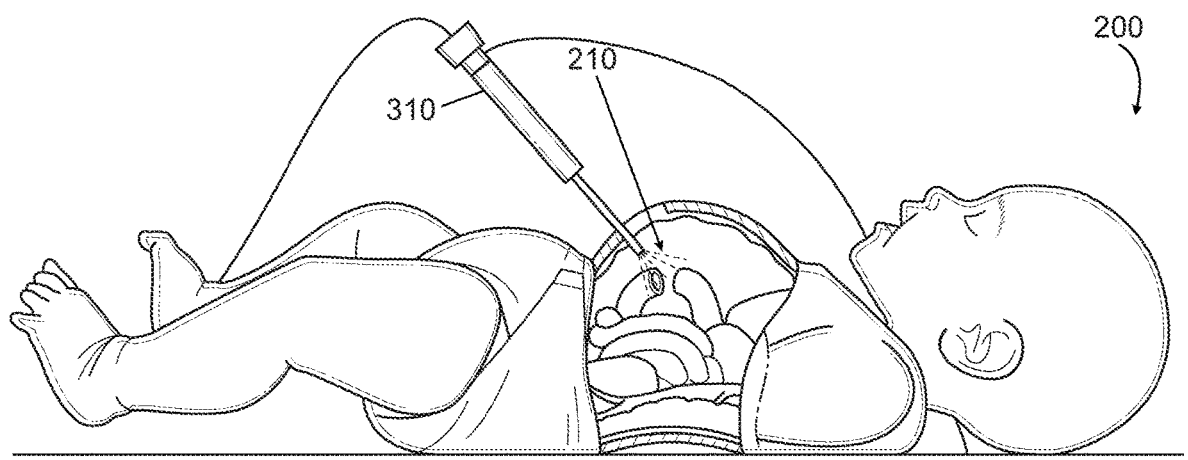
FIG. 1B is a view of a patient with a schematic depiction of a surgical area, with a surgical instrument inserted in the surgical area.
Figure 1C:
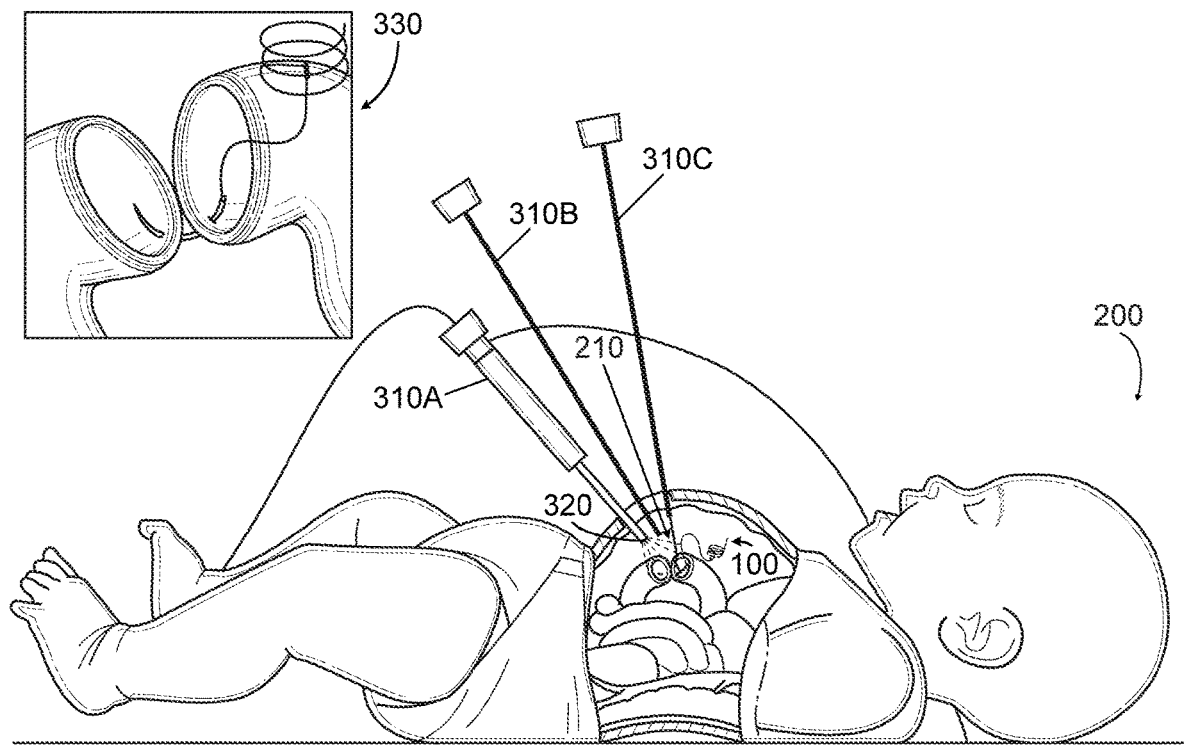
FIG. 1C is a view of a laparoscopic surgery in progress, utilizing the curled suture device of the present invention.

Referring to FIGS. 1A-1D, a laparoscopic surgery using the curled suture device 100 of the present invention is depicted. As shown in FIGS. 1A and 1B, the patient 200 may require a surgical procedure, such as the depicted laparoscopic surgery, and will have a certain surgical cavity 210 wherein the healthcare provider will perform the procedure, inserting various instruments 310 to perform their respective intended functions as needed during the course of the procedure. For instance, as shown in FIG. 1C, the patient 200 with surgical cavity 210 may have instruments 310A, 310B, and 310C inserted into the surgical cavity 210 to set the surgical area in the appropriate manner to enable the healthcare provider to effectively perform the procedure.

Figure 1D:
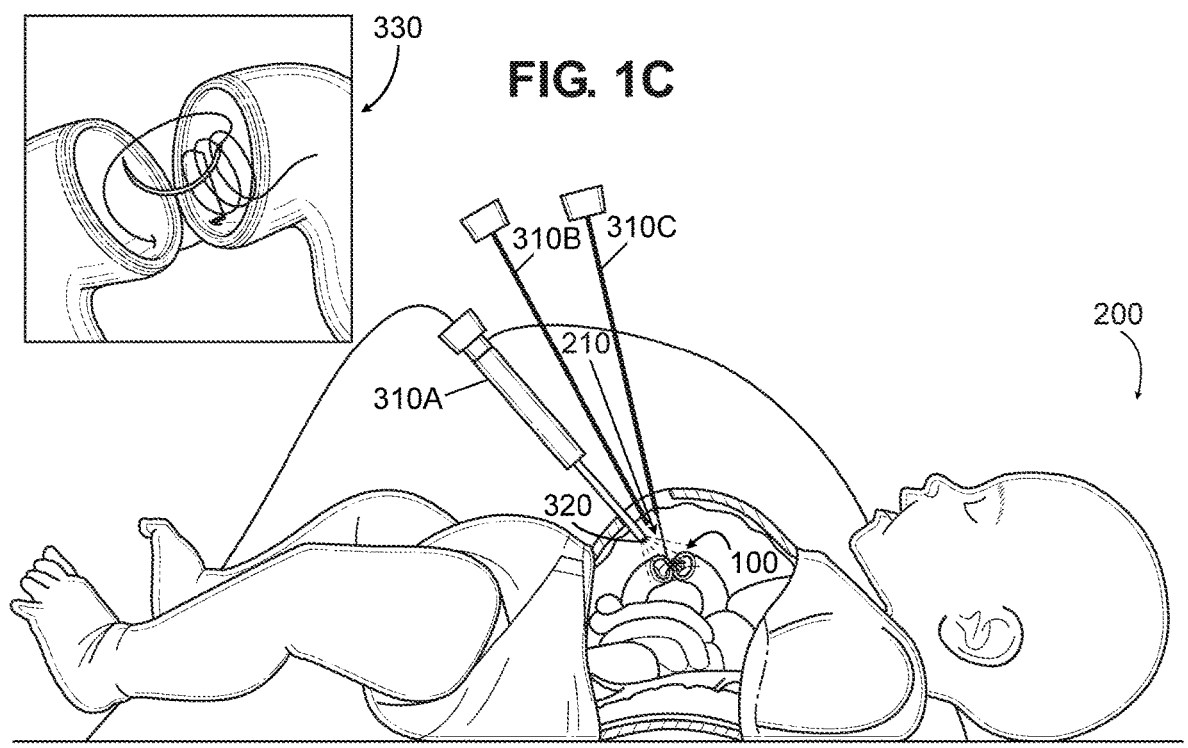
FIG. 1D is a view of a laparoscopic surgery in progress, utilizing the curled suture device of the present invention to create a knot in the surgical area.

As shown in FIGS. 1C and 1D, which depict a typical laparoscopic surgical procedure, there is a camera 320 focused on the appropriate area of the surgical cavity 210. This camera 320 allows the healthcare provider to view the appropriate area of the surgical cavity 210 on a screen 330 formatted to depict the appropriate area of the surgical cavity 210. However, the camera 320 is, by its nature, limited in scope and will only ever be able to depict a limited view of the surgical cavity 210 on the screen 330. Accordingly, if the healthcare provider needs to see additional areas of the surgical cavity 210, he or she will need to continually adjust the various instruments 310 and camera 320 accordingly to view the appropriate area of the surgical cavity 210, which may disrupt the procedure or physicality of the patient 200, or otherwise operate outside the viewing area of the camera 320, which may lead to issues during the procedure.

However, in using the curled suture device 100 of the present invention, the camera 320 is able to present the full scope of the procedure area on the screen 330, with minimal movement of the camera 320 within the surgical cavity 210. For example, as depicted in FIG. 1D, the camera 320 can capture enough of the appropriate area of the surgical cavity 210 so that the screen 330 can depict the entirety of the suturing method of the curled suture device 100. It may be understood by those in the art that this focusing of the camera 320 on a single area of the surgical cavity 210 is facilitated by provision of a suture device that provides for the ready-made knot or multiple ready-made knots on the specially manufactured thread as described herein, and thereby eliminating the need for the healthcare provider to create his or her own knot(s) in the suture in the traditional manner while performing the procedure.

Figure 2C:
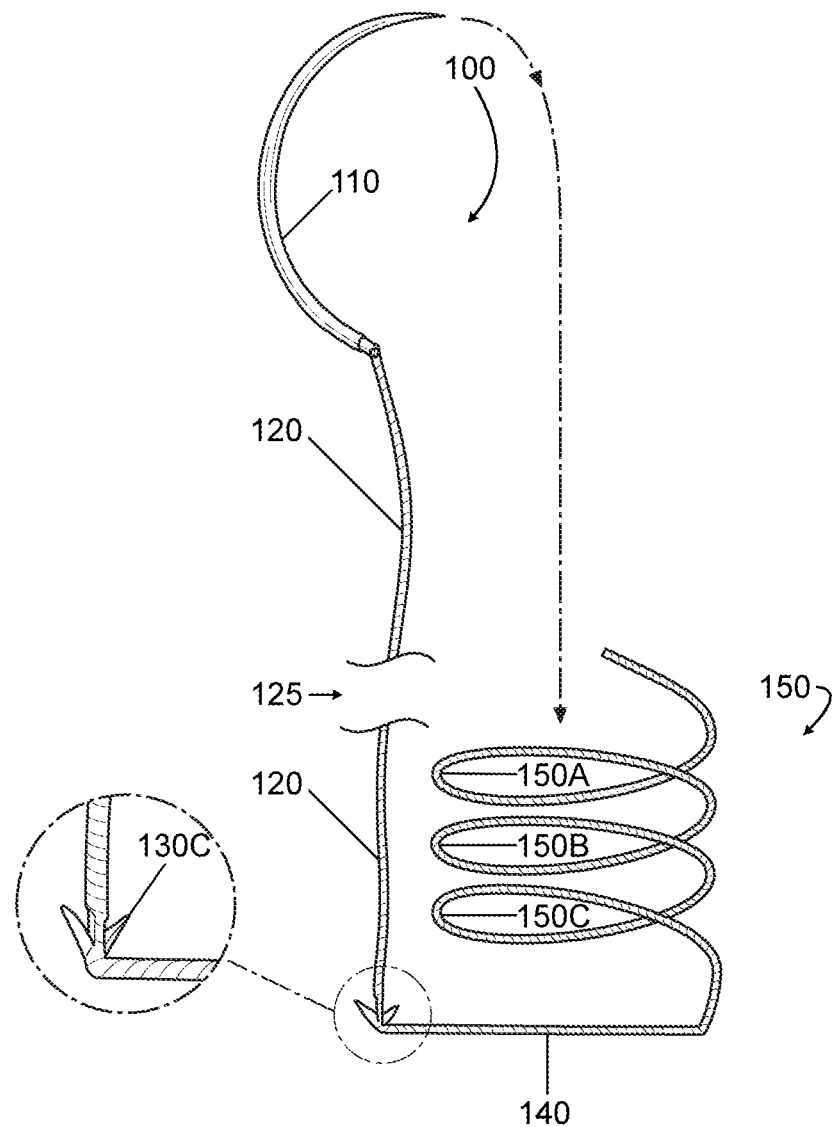
FIG. 2C is a schematic view of the curled suture device according to a third embodiment of the present invention.

Referring now to FIGS. 2A-2C, embodiments of the curled suture device 100 of the present invention feature a needle 110 at one end of the curled suture device 100, and a curled portion of thread 150 at the opposite end of the curled suture device 100 from the needle 110. The thread 120 may be any one of several varied lengths, so that the healthcare provider or suturing professional may select the appropriately-sized curled suture device 100 as needed for a specific procedure. For example, it is known in the art that a healthcare provider may use a suture device that is 36", or 90 cm, long for one procedure, or a shorter 6", or 15 cm, suture device for a different procedure. However, in all instances in the prior art, the suture device must be several inches long to allow sufficient room for the healthcare provider to thread the appropriate tissue and appropriately knot the suture during and at the completion of the procedure to ensure that the tissue is appropriately mended. Accordingly, although the curled suture device 100 of the present invention may have a thread 120 of varied lengths, such that the illustrative gap 125 pictured in the FIGS. 2A-2C may illustrate several varied lengths, the curled suture device 100 will almost always feature a thread 120 of a length shorter than a corresponding suture device without a set of curls 150, which would require additional length to prepare and create a knot in the final step of suturing the tissue.

Thread 120 may be comprised of any one of varied materials that are generally available as suturing thread materials. For example, thread 120 may be a polypropylene suture like PROLENE, which is a non-absorbable surgical suture. Other examples of a non-absorbable surgical suture are polyester sutures like ETHIBOND or nylon sutures like ETHILON or NUROLON. Such a non-absorbable suture may be preferable in certain surgical procedures when the healthcare provider requires a thread that will be stronger and longer-lasting than other absorbable threads, such as in cardiovascular procedures. Alternatively, thread 120 may be made of an absorbable thread, such as, without limitation, a poliglecaprone suture like MONOCRYL, a polyglactin suture like VICRYL, or a polydioxanone suture like PDS II. Such a suture may be preferable in certain procedures when it is preferable that the suture ultimately break down within the patient's body within a certain period of time. For example, certain absorbable threads may be broken down and absorbed within the patient's body in as little as two weeks, or may last over a year. However, such absorbable sutures are not preferable in procedures wherein the suture is meant to not only mend, but permanently connect, two pieces of tissue, such as repairing stitches for blood vessels or in cardiovascular or neurological procedures. The curled suture device 100 of the present invention is not meant to be limited to one type of thread 120, but may be available as either an absorbable thread or non-absorbable thread, so that the healthcare provider may select the appropriate type of curled suture device 100 based in part on the type of thread 120 featured in the curled suture device 100.

Additionally, thread 120 may be of either a braided or non-braided type. If thread 120 is braided, it may feature a number of strands woven together like a string. Such a braided thread, which may be made of a polyester, silk, or other material, would provide additional grip for the suture and may be stronger than a non-braided thread. However, a non-braided thread may be preferable as the thread 120 of the curled suture device 100 because it may be less prone to becoming infected, and may provide for a smoother surgical procedure within the body. Thread 120 of the curled suture device 100 of the present invention may be of either this braided or non-braided variety, so that the healthcare provider may select the appropriate type of curled suture device based in part on whether the thread 120 is braided or non-braided.

The needle 110 of the curled suture device 100 may also be provided in different embodiments. Suture needles are generally of four types: a cutting needle, a reverse cutting needle, a tapered needle, or a reverse tapered needle. Needle 110 of the curled suture device may be either cutting, reverse cutting, tapered, or reverse tapered, such that the healthcare provider may select the appropriate type of curled suture device based in part on whether the needle 110 is a cutting, reverse cutting, tapered, or reverse tapered needle.

Referring back to FIGS. 2A-2C, the curled suture device 100 features, at the end opposite the needle 110, an end section comprising a set of a curled portion of thread 150, an angled, semi-rigid portion of thread 140 directly before a curled portion of thread 150, and a stopper mechanism 130 featured immediately prior to the semi-rigid portion of thread 140, such that the semi-rigid portion of thread 140 acts as an intermediary feature between the stopper 130 and the curled portion of thread 150. It may be appreciated that some threads may be comprised of a flexible type of material, such as silk, to account for the surgical considerations discussed above. In such an instance, the semi-rigid portion of thread 140 may feature an additional coating of material with a a semi-rigid character, such as, but not limited to, plastic or poliglecaprone, to ensure that the semi-rigid portion of thread 140 retains a semi-rigid configuration.

As shown in FIG. 2A, the curled suture device 100 may feature a stopper mechanism 130 that comprises an additional layer of material 130A directly overlaid on the suture thread, and directly adjacent the angled, semi-rigid portion of thread 140. When the curled suture device 100 is pulled through a piece of tissue, the additional layer of material 130A will act as a stopper for the curled suture device because the area of the suture thread overlaid with the additional layer of material 130A is accordingly thicker than the main portion of thread 120. It therefore cannot be pulled through the tissue as easily as thread 120, and would require significant extra effort to be pulled through the tissue being sutured. Accordingly, when needle 110 is pulled through a piece of tissue, the main portion of thread 120, up to additional layer of material 130A, will be pulled through the piece of tissue, but the semi-rigid portion of thread 140 and the curled portion of thread 150 will remain on the first side of the tissue due to the action of the additional layer of material 130A. It may be preferable that this additional layer of material 130A is featured on a non-absorbable suture thread, as it may otherwise interfere with an absorbable suture thread breaking down in the body appropriately, as discussed above.

A stopper knot 130B, pictured in FIG. 2B, functions in much the same manner as the additional layer of material 130A. The stopper knot 130B is featured directly adjacent the angled, semi-rigid portion of thread 140, such that the semi-rigid portion of thread 140 acts as an intermediary feature between the stopper knot 130B and the curled portion of thread 150. The stopper knot 130B is configured such that when needle 110 and thread 120 are pulled through a piece of tissue, the stopper knot 130B will halt the progress of the thread 120 through the piece of tissue. The stopper knot 130B, semi-rigid portion of thread 140, and curled portion of thread 150 will therefore remain on the first side of the tissue, ready for the creation of the suture knot, discussed in more detail below. It may be preferable that this stopper knot 130B is featured on an absorbable suture thread, as it would be created with the same material as the absorbable suture thread and would thus break down in the body appropriately, according to the requirements of the absorbable suture thread selected for the procedure, as discussed above.

A barb configuration 130C, pictured in FIG. 2C, functions in much the same manner as the additional layer of material 130A and the stopper knot 130B. The barb configuration 130C is featured directly adjacent an angled, semi-rigid portion of thread 140, such that the semi-rigid portion of thread 140 acts as an intermediary feature between the barb configuration 130C and the curled portion of thread 150. The barb configuration 130C is configured such that when needle 110 and thread 120 are pulled through a piece of tissue, the barb configuration 130C will halt the progress of the thread 120 through the piece of tissue by catching onto the piece of tissue. The barb configuration 130C, semi-rigid portion of thread 140, and curled portion of thread 150 will therefore remain on the first side of the tissue, ready for the creation of the suture knot, discussed in more detail below. It may be preferable that this barb configuration 130C is featured on an absorbable suture thread, as it would be created with the same material as the absorbable suture thread and would thus break down in the body appropriately, according to the requirements of the absorbable suture thread selected for the procedure, as discussed above.

It may be appreciated that a stopper mechanism 130 may take a variety of forms, not meant to be limited to the additional layer of material 130A, stopper knot 130B, or barb configuration 130C discussed above. For example, a stopper mechanism may be a portion of thread configured with a variety of different jagged edges, knots, or additional materials that can halt the progress of the thread.

As shown in FIGS. 2A-2C, the curled portion of thread 150 may include, without limitation, a first curl 150A, a second curl 150B, and a third curl 150C. To appropriately create a knot, as discussed below, the curled portion of thread 150 should at least comprise a first curl 150A and a second curl 150B, and preferably a third curl 150C as well. However, it is to be understood that the curled portion of thread 150 may include additional curls, such as a fourth or fifth curl, to allow for a larger or more secure knot, which may be preferable by the healthcare provider in some procedures.

It may be further appreciated that the present invention's ready-made knot configuration, comprising of the angled, semi-rigid portion of thread 140 and the curled portion of thread 150, may be specially manufactured such that the first combination of semi-rigid portion of thread 140 and curled portion of thread 150 are pre-existing on the curled suture device 100, as depicted in FIGS. 2A-2C, but additional semi-rigid portions of thread and corresponding curled portions of thread are automatically formed upon creation of a knot from a previous combination thereof, allowing for multiple knots. The preferred embodiment of the present invention encompassing of these additional ready-made knot configurations will be described below.

Figure 3A:
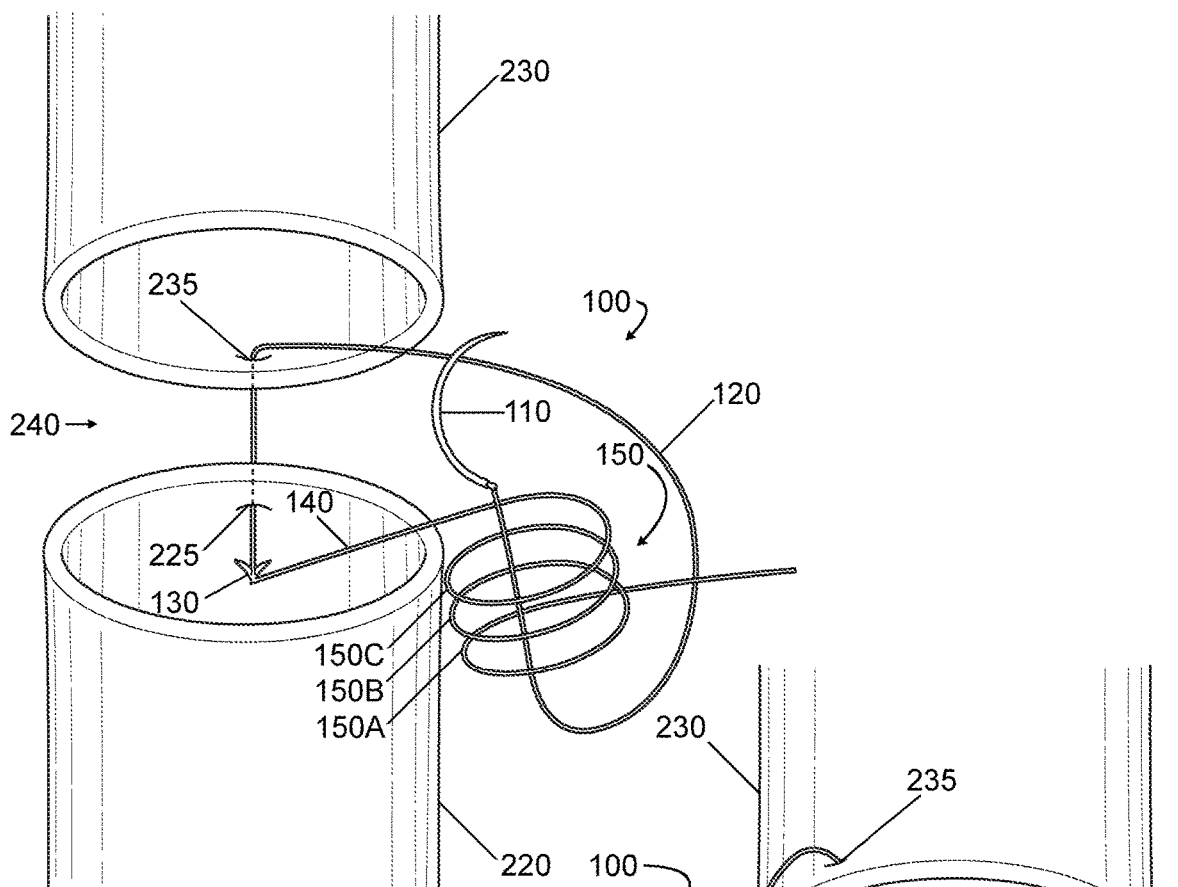
FIG. 3A is a detailed view of the method of suturing two pieces of tissue by using the curled suture device of the present invention, as beginning from the interior of the first tissue.
Figure 3B:
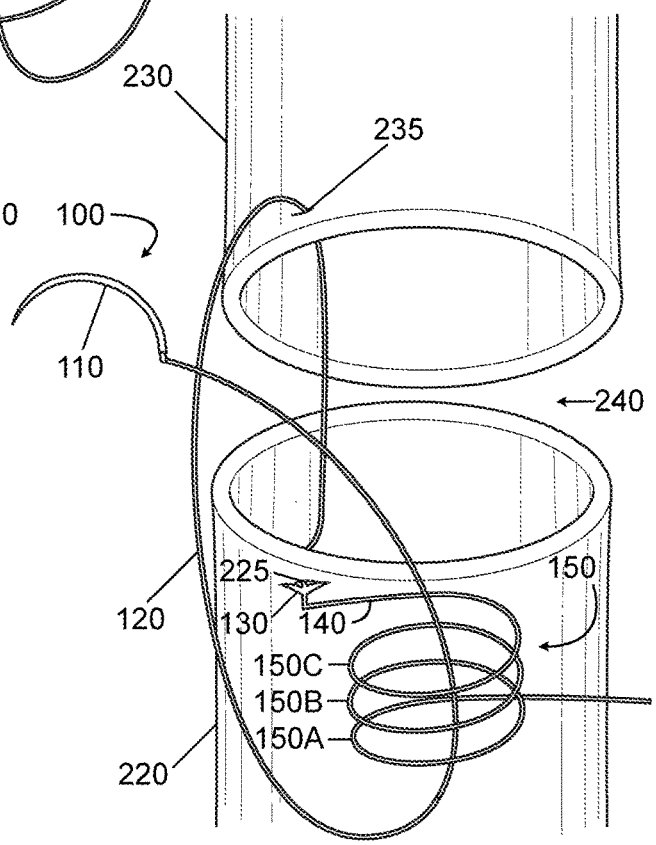
FIG. 3B is a detailed view of the method of suturing two pieces of tissue by using the curled suture device of the present invention, as beginning from the exterior of the first tissue.

Referring now to FIGS. 3A and 3B, the method of suturing using the curled suture device 100 of the present invention is depicted in part. As illustrated in FIG. 3A, the needle 110 may be inserted through the first piece of tissue 220 to create a first hole 225 in the first piece of tissue 220, beginning from an inside approach. Thereafter, the needle 110 is then inserted in the second piece of tissue 230 such that second hole 235 is created in the second piece of tissue 230. Alternatively, as illustrated in FIG. 3B, depending on the positioning of the first piece of tissue 220 and second piece of tissue 230 relative to the healthcare provider, the needle 110 may be inserted through the first piece of tissue 220 to create a first hole 225 in the first piece of tissue 220, beginning from an outside approach. Thereafter, the needle 110 is then inserted in the second piece of tissue 230 such that second hole 235 is created in the second piece of tissue 230. Nonetheless, the needle 110 of the curled suture device 100 thus connects the first and second pieces of tissue in a typical manner of suturing.

It may be understood that although FIGS. 3A and 3B depict two pieces of tissue relatively near each other, close enough together that the needle 110 may be connected to both the first piece of tissue 220 and second piece of tissue 230 at the same time, the first and second pieces of tissue 220 and 230 may be of such a distance apart from one another that the thread 120 of the curled suture device may be connecting the first and second pieces of tissue 220 and 230 together as the needle 110 is in the process of creating the first and second holes 225 and 235 at the outset of suturing.

Figure 4:
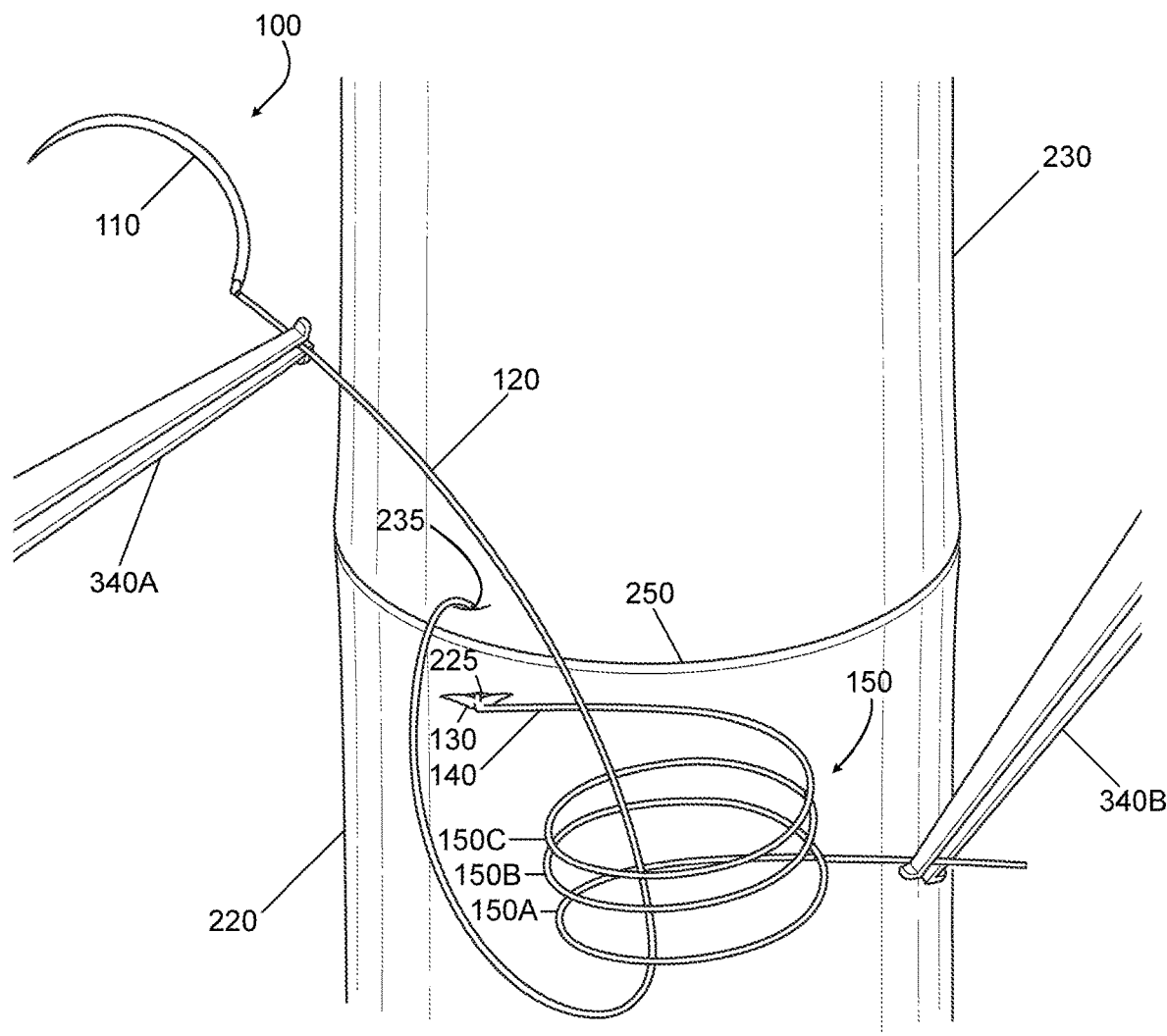
FIG. 4 is a detailed view of the method of suturing two pieces of tissue by using the curled suture device of the present invention, whereby the pieces of tissue become bound.

Referring now to FIG. 4, in conjunction with previous FIGS. 3A and 3B, the depiction of the method of suturing using the curled suture device 100 of the present invention is continued in part. As illustrated, upon the above-described piercing of the first piece of tissue 220 and second piece of tissue 230 by the needle 110, whether from the inside or outside of the tissue as described above, the suturing method will further consist of the needle 110 being pulled by a first of a pair of forceps 340A. A second pair of forceps 340B will be simultaneously holding the opposite end of thread, at such a distance that the stopper mechanism 130 of the curled suture device 100 is utilized. As a result, any gap 240, as shown in previous FIGS. 3A and 3B, between the first piece of tissue 220 and the second piece of tissue 230, is forced closer together at a connection area 250. It may be appreciated that when the stopper mechanism 130 of the curled suture device 100 is adjacent the first hole 225 in the first piece of tissue 220, the thread 120 will no longer be pulled through the first hole 225 in the first piece of tissue 220. Instead, the first piece of tissue 220 will be pulled closer to second piece of tissue 230, minimizing the gap 240 between the first and second pieces of tissue 220 and 230 to form a connection area 250. Additionally, any ready-made knot configuration(s), such as the depicted angled, semi-rigid portion of thread 140 and the curled portion of thread 150, of the curled suture device 100 will not be pulled through the first hole 225 in the first piece of tissue 220, but will instead remain intact outside the first piece of tissue 220.

When the first and second pieces of tissue 220 and 230 are pulled together, as illustrated in FIG. 4 and described above, the angled, semi-rigid portion of the thread 140 remains on the outside of the first piece of tissue 220. This straight portion of the thread 140 thereby provides a space for the curled portion of the thread 150 to be more easily accessible by the healthcare provider in creating a desired knot.

As illustrated in FIGS. 3A, 3B, and 4, the method of suturing using the curled suture device 100 of the present invention comprises of the healthcare provider leading the needle 110 out of the second piece of tissue 230 through the curled portion of thread 150 featured on the outside of the first piece of tissue 220. The healthcare provider leads the needle 110 first through the first curl 150A, the furthest curl from the semi-rigid portion of thread 140, and then leads the needle 110 through the second curl 150B, the third curl 150C, and any additional curls that may be featured in the curled portion of thread 150.

Figure 5:
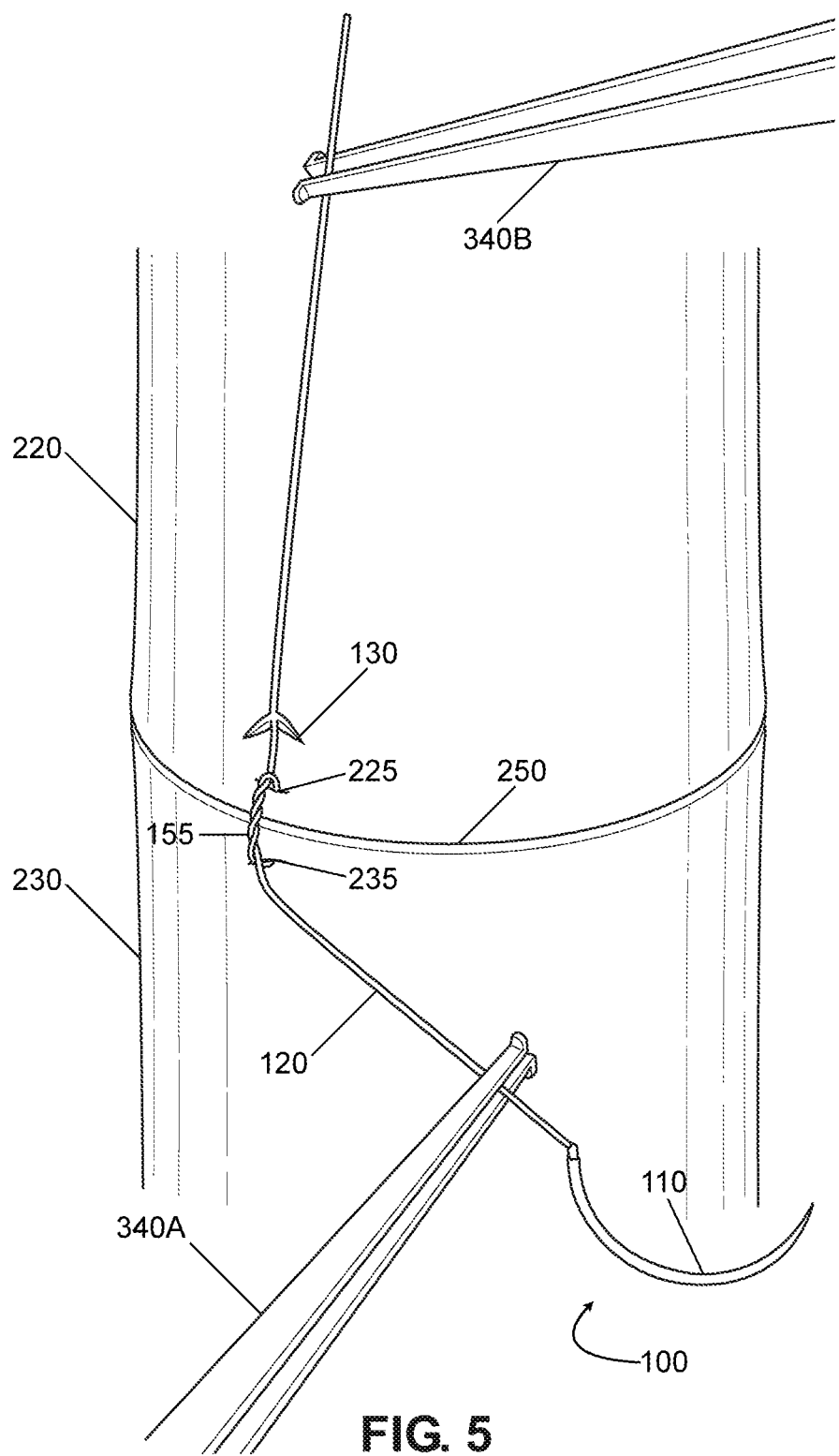
FIG. 5 is a detailed view of the method of suturing two pieces of tissue by using the curled suture device of the present invention, formulating a first knot binding the pieces of tissue.

Referring now to FIG. 5, the depiction of the method of suturing using the curled suture device 100 of the present invention is continued in part. Here, the first knot 155 in the curled suture device 100 is created upon the healthcare provider's pulling of the needle 110 by use of the first of the pair of forceps 340A, while pulling the opposite end of the thread 120 with the second of the pair of forceps 340B, after the needle 110 was guided through the curled portion of the thread 150, as depicted in FIG. 4 and described above. While creating the knot in the curled suture device 100, the pulling motion of the needle 110 with the pair of forceps 340, and accordingly the thread 120, will also effectively close the gap 240 between the first and second pieces of tissue 220 and 230. As a result, the first and second pieces of tissue 220 and 230 are pulled adjacent to each other to create the desired connection area 250, as required by the procedure, and the first knot 155 is thereby holding the suture in place.

Figure 6:
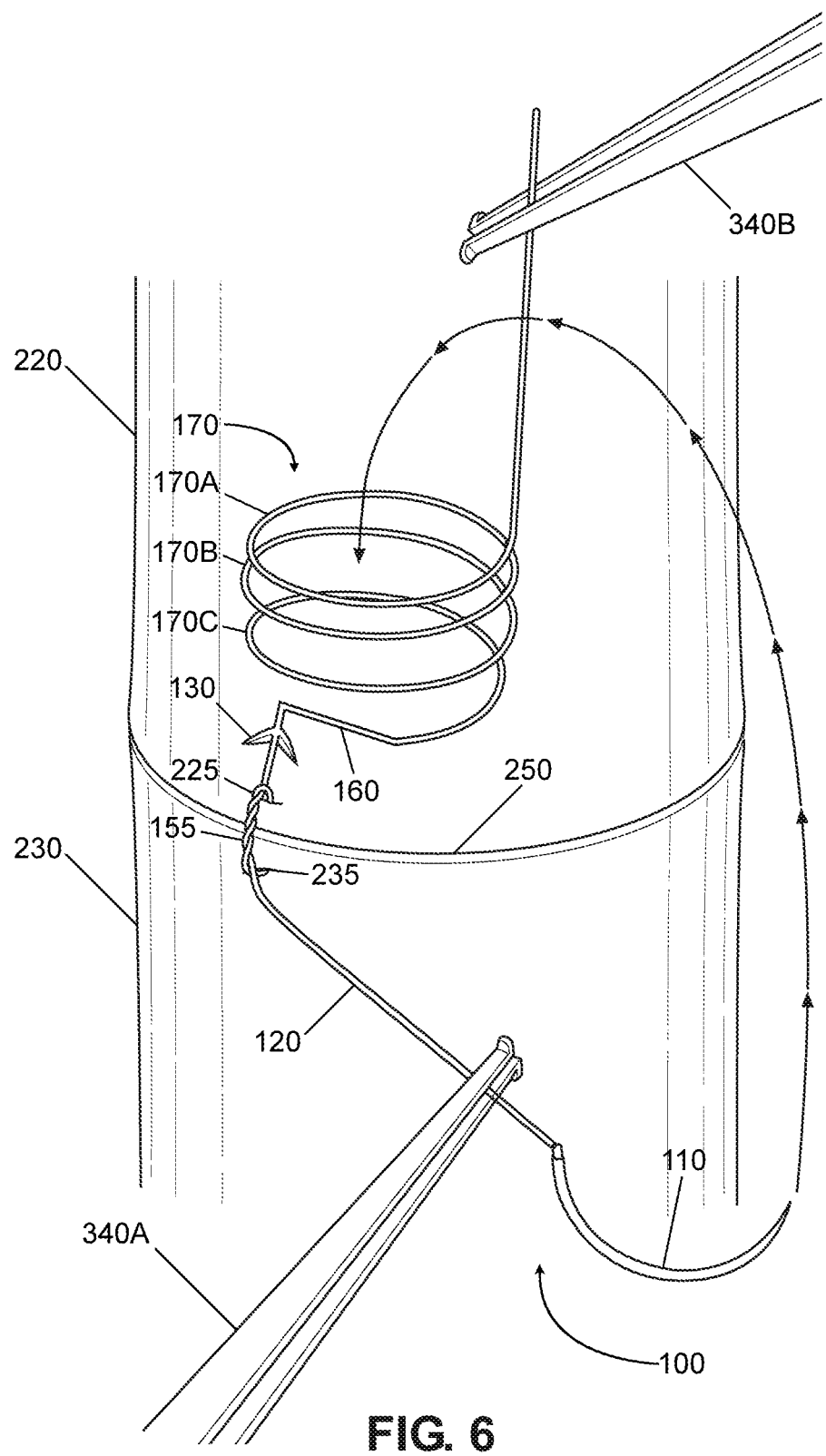
FIG. 6 is a detailed view of the method of suturing two pieces of tissue by using the curled suture device of the present invention, formulating a second knot to bind the pieces of tissue.

Referring now to FIG. 6, the depiction of the method of suturing using the curled suture device 100 of the present invention is further continued in part. Here, upon creation of the first knot 155, the healthcare provider may relax the second of the pair of forceps 340B so as to allow the thread 120 to automatically form a second ready-made knot, consisting of a second angled, semi-rigid portion of thread 160 and a corresponding second curled portion of thread 170 outside the first piece of tissue 220. This additional ready-made knot configuration allows for the creation of an additional knot in the curled suture device 100 of the present invention in much the same way the first knot 155 was created. Here, the second angled, semi-rigid portion of the thread 160 provides a space for the curled portion of the thread 170 to be easily accessible by the healthcare provider in creating the desired knot. Accordingly, the healthcare provider can lead the needle 110 through the second curled portion of thread 170 by use of the first of the pair of forceps 340A. The healthcare provider specifically leads the needle 110 first through the first curl 170A, the furthest curl from the second angled, semi-rigid portion of thread 160, and then leads the needle 110 through the second curl 170B, the third curl 170C, and any additional curls that may be featured in the second curled portion of thread 170.

Figure 7:
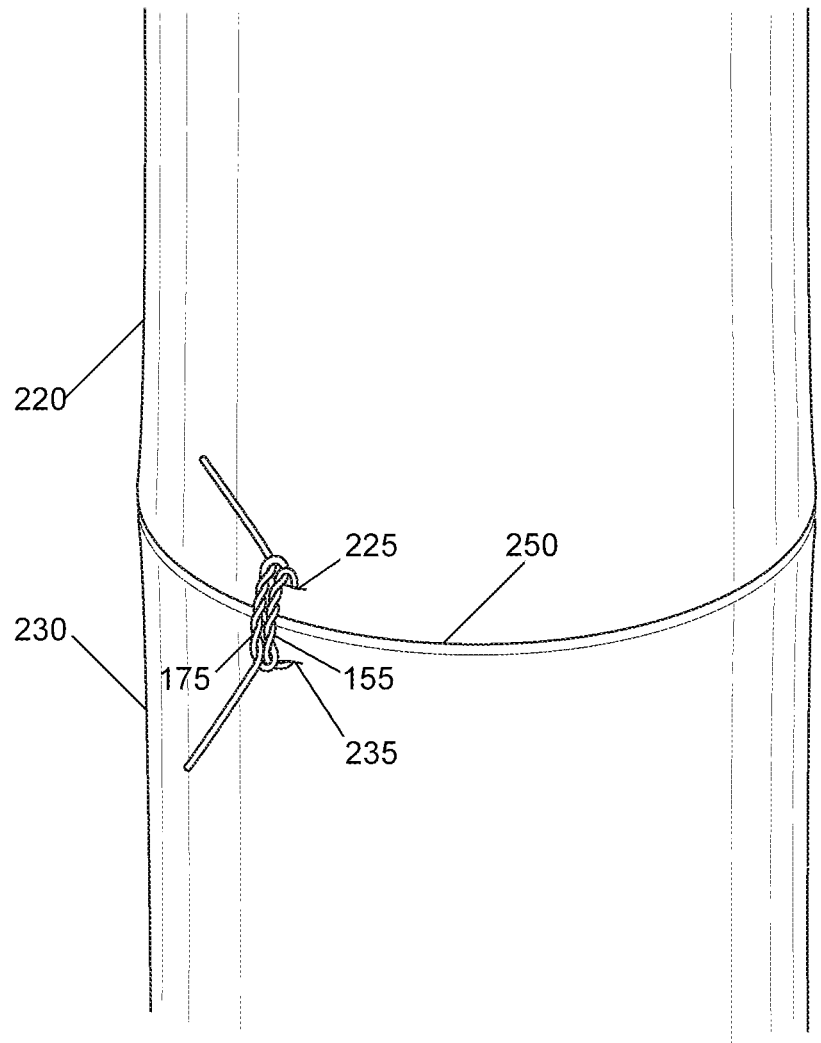
FIG. 7 is a detailed view of the resulting combination of the two knots binding the pieces of tissue by use of the curled suture device of the present invention.

The healthcare provider thereafter can create the second knot 175, as shown in FIG. 7, by the pulling of the needle 110 by use of the first of the pair of forceps 340A, while also pulling the opposite end of the thread 120 with the second of the pair of forceps 340B, after the needle 110 was guided through the second curled portion of the thread 170 as depicted in FIG. 5. The creation of this second knot 175, alongside the first knot 155, will create additional friction in the suture to further secure the connection area 250 between the first and second pieces of tissue 220 and 230, as may be required by the procedure, and the first and second knots 155 and 175 are thereby securely holding the suture in place.

Figure 8:
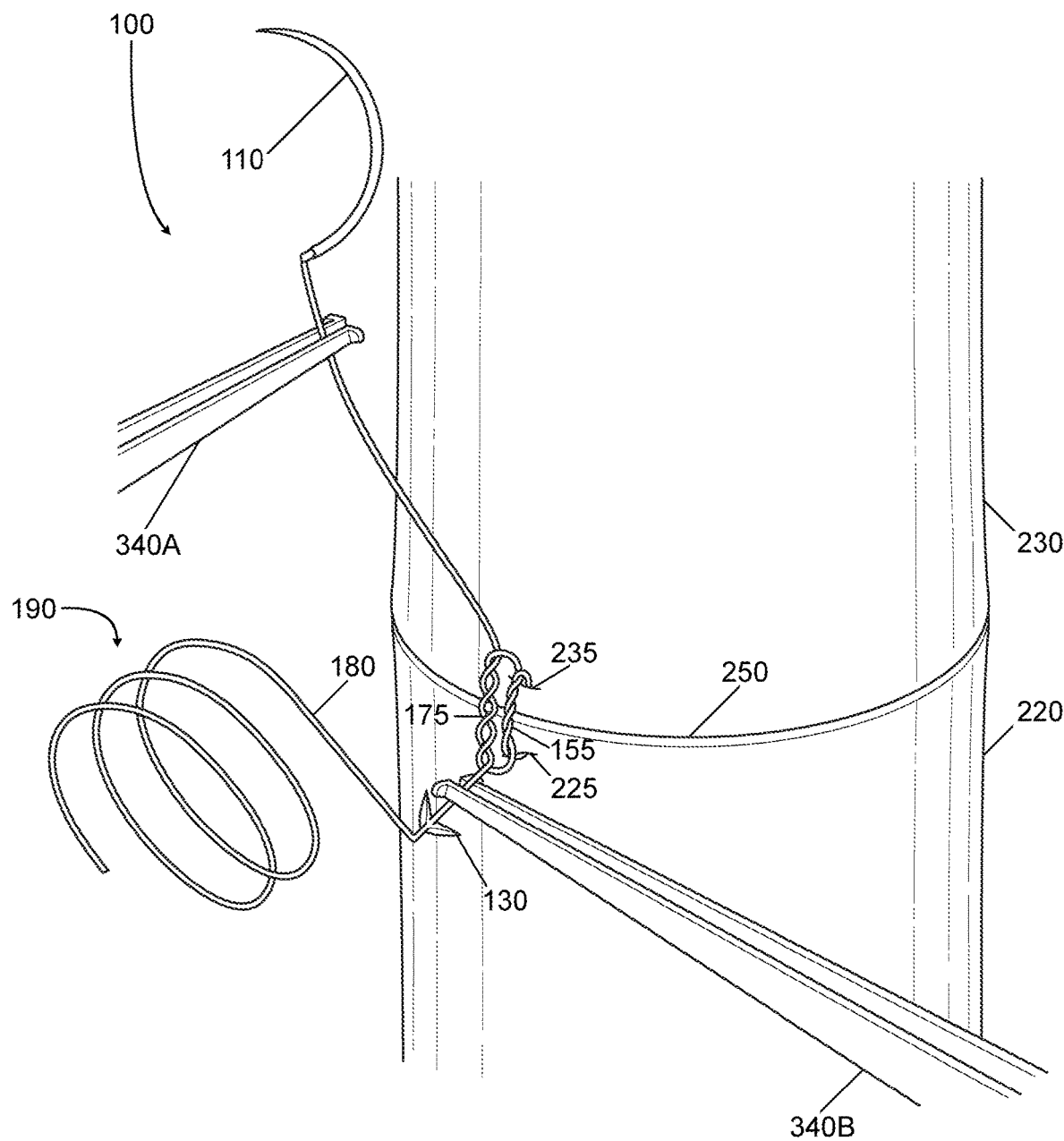
FIG. 8 is a detailed view of the resulting combination of the two knots binding the pieces of tissue by use of the curled suture device of the present invention that allows for an additional knot to bind the pieces of tissue with additional friction.

Accordingly, if satisfied with the result of the created suture, the healthcare provider may cut the excess thread and needle of the curled suture device 100. Otherwise, as shown in FIG. 8, the healthcare provider may desire more friction amongst the first knot 155 and second knot 175 of the suture by creating another knot in the curled suture device 100 of the present invention by, again, relaxing the second of the pair of forceps 340B so as to allow the thread 120 to form a third ready-made knot consisting of a third angled, semi-rigid portion of thread 180 and a corresponding third curled portion of thread 190 outside the first piece of tissue 220. This additional ready-made knot allows for the creation of another knot in the curled suture device 100 in the same way the second knot 175 was created.

It may be appreciated that by using the curled suture device 100 of the present invention, the healthcare provider may effectively suture the appropriate tissue with only one hand, given that he is not required to create a knot in the suture by other means. Accordingly, if, while suturing, the healthcare provider realizes that the upcoming knot is not in an appropriate location, the healthcare provider may easily adjust the location of the suture and upcoming knot within the surgical cavity. Such an adjustment is facilitated by use of the curled suture device 100 and its ready-made knots in part because the healthcare provider is able control the movement of both the curled suturing device 100 and tissue 220 or 230 with only one hand.

It may also be appreciated in effectively suturing the appropriate tissue with only one hand operating the curled suture device 100, the curled suture device 100 thereby decreases the instruments and crowding that takes places in a laparoscopic surgical procedure using the suture devices presently available in the art. Moreover, the curled suture device 100 also focuses the surgical area of the procedure on the area featuring the curled portions of thread 150, 160, and/or 170, such that the healthcare provider may more effectively utilize his or her available viewing area, which is typically limited in a laparoscopic procedure, as discussed above and depicted in FIGS. 1C and 1D.

Many changes and modifications can be made in the present invention without departing from the spirit thereof. I therefore pray that my rights to the present invention be limited only by the scope of the appended claims.

I claim:
1. A suture device, comprising:
(i) a needle; and
(ii) a thread attached to said needle, the thread having a proximate end portion and distal end portion, the distal end portion including a shape-memory material and being adapted to shift between a first, curled configuration resembling a corkscrew and a second configuration, wherein the distal end portion straightens when tying a knot in the thread, and wherein the distal end portion biases to the first configuration to allow tying of additional knots in the thread; and wherein the thread further comprises a stopper formed by an additional tubular layer of material, a knot, or a barb and a semi-rigid portion formed between the stopper and the distal end position, the semi-rigid portion extending at an angle to the stopper.

2. The device of claim 1, wherein the needle is a cutting needle, reverse cutting needle, tapered needle, or reverse tapered needle.

3. The device of claim 1, wherein the thread is an absorbable suture thread.

4. The device of claim 1, wherein the thread is a braided suture thread.

\* \* \* \* \*